(12) United States Patent
Kamal et al.

(10) Patent No.: US 6,951,853 B1
(45) Date of Patent: Oct. 4, 2005

(54) PROCESS FOR PREPARING PYRROLO[2, 1-C] [1,4] BENZODIAZEPINE HYBRIDS

(75) Inventors: Ahmed Kamal, Andhra Pradesh (IN); Ramulu Poddutoori, Andhra Pradesh (IN); Srinivas Olepu, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 32 days.

(21) Appl. No.: 10/812,842

(22) Filed: Mar. 30, 2004

(51) Int. Cl.[7] ..................... C07D 487/00; A61K 31/55; A61P 35/00
(52) U.S. Cl. ...................... 514/220; 540/496
(58) Field of Search ........................ 514/220; 540/496

(56) References Cited

U.S. PATENT DOCUMENTS 6,362,331 B1 * 3/2002 Kamal et al. ............... 540/497

FOREIGN PATENT DOCUMENTS

WO        00/12508        3/2000

OTHER PUBLICATIONS

Thurston, David E. et al. "Synthesis of Sequence–Selective C8–Linked Pyrrolo[2,1–c][1,4]benzodiazepine DNA Interstrand Cross–Linking Agents", *J. Org. Chem.* (1996), 61, pp 8141–8147.

Kamal, Ahmed et al. "Design, Synthesis and Evaluation of New Noncross–Linking Pyrrolobenzodiazepine Dimers with Efficient DNA Binding Ability and Potent Antitumor Activity", *J. Med. Chem.* (2002), 45, pp 4679–4688.

Sun, Qun et al. "Structure Activity of Topoisomerase I Poisons Related to Hoechst 33342", *Bioorganic & Medicinal Chemistry Letters* (1994), vol. 4, No. 24, pp 2871–2876.

Kelly, David P. et al. "DNA Binding Compounds. VI. Synthesis and Characterization of 2,5'–Disubstituted Bibenzimidazoles Related to the DNA Minor Groove Binder Hoechst 33258", *Aust. J. Chem.* (1994), 47, pp 1751–1769.

Thurston, David E. and D. Subhas Bose. "Synthesis of DNA–Interactive Pyrrolo[2,1–c][1,4]benzodiazepines", *Chem. Rev.* (1994), 94, pp 433–465.

Tawar, Urmila et al. "Influence of Phenyl Ring Disubstitution on Bisbenzimidazole and Terbenzimidazole Cytotoxicity: Synthesis and Biological Evaluation as Radioprotectors", *J. Med. Chem.* (2003), 46, pp 3785–3792.

Turner, Paul R. and William A. Denny. "The mutagenic properties of DNA minor–groove binding ligands", *Mutation Research* (1996), 355, pp 141–169.

* cited by examiner

*Primary Examiner*—Bruck Kifle
(74) *Attorney, Agent, or Firm*—Ladas & Parry LLP

(57) ABSTRACT

Novel pyrrolo[2,1-c][1,4]benzodiazepine hybrids as well as processes for the preparation of novel pyrrolo[2,1-c][1,4] benzodiazepine hybrids are dislcosed. More particularly, present invention relates to a process for the preparation of novel pyrrolo[2,1-c][1,4]benzodiazepine hybrids as DNA sequence selective agents which are useful as potential antitumour agents. In particular, the present invention relates to a process for the preparation of new pyrrolo[2,1-c][1,4] benzodiazepine hybrids as potential antitumour agents. These compounds have the formula XIV shown below:

(XIV)

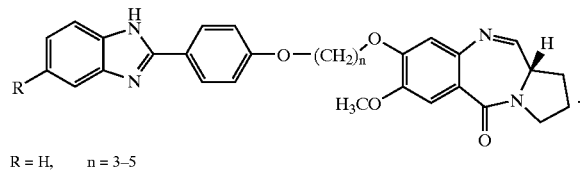

R = H,    n = 3–5

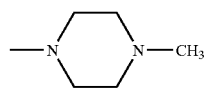

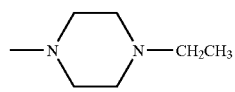

18 Claims, No Drawings

PROCESS FOR PREPARING PYRROLO[2, 1-C] [1,4] BENZODIAZEPINE HYBRIDS

FIELD OF THE INVENTION

The present invention relates to novel pyrrolo[2,1-c][1,4] benzodiazepine hybrids as well as processes for the preparation of novel pyrrolo[2,1-c][1,4]benzodiazepine hybrids. More particularly, present invention relates to a process for the preparation of novel pyrrolo[2,1-c][1,4]benzodiazepine hybrids as DNA sequence selective agents which are useful as potential antitumour agents. In particular, the present invention relates to a process for the preparation of new pyrrolo[2,1-c][1,4]benzodiazepine hybrids as potential antitumour agents.

BACKGROUND OF THE INVENTION

Pyrrolo[2,1-c][1,4]benzodiazepine antitumour antibiotics are commonly known as anthramycin class of compounds. In the last few years, a growing interest has been shown in the development of new pyrrolo[2,1-c]benzodiazepines (PBDs). These antibiotics react covalently with DNA to form an N2-guanine adduct that lies within the minor groove of duplex DNA via an acid-labile animal bond to the electrophilic imine at the N10-C11 position (Kunimoto, S.; Masuda, T.; Kanbayashi, N.; Hamada, M.; Naganawa, H.; Miyamoto, M.; Takeuchi, T.; and Unnezawa, H. J. Antibiot., 1980, 33, 665.; Kohn, K. w. and Speous, C. L. J. Mol., Biol., 1970, 51, 551.; Hurley, L. H.; Gairpla, c. and Zmijewski, M. Biochem, Biophys. Acta., 1977, 475, 521,; Kaplan, D. J. and Hurley, L. H. biochmestry, 1981, 20, 7572). The molecules have a right-handed twist, which allows them to follow the curvature of the minor groove of B-form double-stranded DNA spanning three base pairs. Recently, PBD dimmers have been developed that comprises two C2-exo-methylene substituted DC-81 subunits tethered through their C-8 position I an inert propanedioxy linker (Gregson, S. J.; Howard, P. W; Hartely, J. A.; Brooks, N. a.; Adams, L. J.; Jenkins, T. C.; Kelland, L. R. and Thurston, D. E. J. Med Chem. 2001, 44, 737). A recent development has been the linking of two PBD units through their C-8 positions to give bisfunctional alkylating agents capable of cross-linking DNA (Thurston, D. E.; Bose, D. S.; Thomson, a, S; Howard, P. W.; Leoni, A; Croker, S. J; Jenkins, T. C.; Neidle, S. and Hurley, L. H. J. Org. Chem., 1996, 61, 8141). Recently, a noncross linking mixed inmine-amide PBD dimmers have been synthesized that have significant DNA binding ability and potent anti tumour activity. (Kamal, A,; Ramesh, G.; Laxman, N; Ramulu, P,; Srinicas, O.; Neelima, K.; Kondapi, A. K.; Srinu, V. B,; Nagarajaram, H. M. J. Med. Chem. 2002, 45, 4679). These imine-amide PBD dimers have the structures shown below:

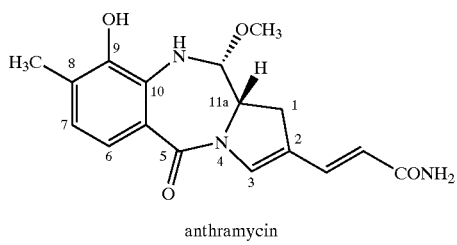

anthramycin

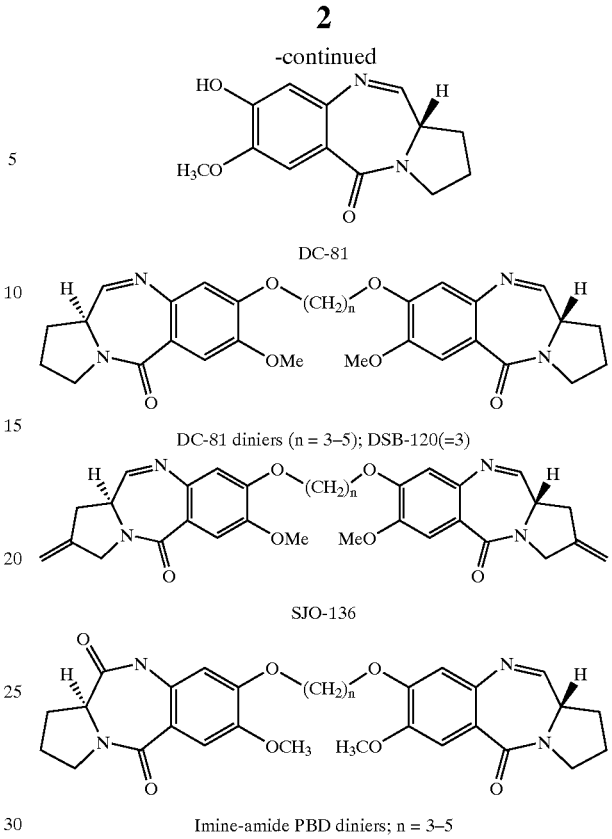

Naturally occurring pyrrolo[2,1-c][1,4]benzodiazepines belong to a group of antitumour antibiotics derived from *Streptomyces* Species. Recently, there is much impetus for the PBD system as they can recognize and bind to specific sequence of DNA. Examples of naturally occurring PBDs include anthramycin, DC-81, tomaymycin, sibiromycin and neothramycin.

However, the clinical efficacy for these antibiotics is hindered by several limitations, such as poor water solubility, cardiotoxicity, development of drug resistance and metabolic inactivation. There is therefore, a urgent need for such antibiotics which do have the disadvantages of the prior art.

OBJECTS OF THE INVENTION

It is therefore am important object of the present invention is to provide a new pyrrolo[2,1-c][1,4]-benzodiazepine hybrids useful as antitumour agents.

Another object of the present invention is to provide a process for the preparation of novel pyrrolo[2,1-c][1,4]-benzodiazepine hybrids useful as antitumour agents.

SUMMARY OF THE INVENTION

The above and othe objects of the present invention are achieved by providing a novel pyrrolo[2,1-c][1,4] benzodiazepine hybrid compound. The present invention also provides a process for the preparation of 7-methoxy-8-{n-[41H-benzo[d]imidazolo-2ylphenoxy]alkyl}-oxy (11aS)1,2,3-11atetrahydro-5H-pyrrolo[2,1-c]1,4] benzodiazepin-5 one V, 7-methoxy-8-(n-{4-[6-(4-methyl hexahydro-1-pyrainyl)-1H-benzo[d]imidazol-2yl] phenoxy}alkyl-oxy-(11-aS)-1,2,3,11a-tetrahydro-5H- pyrrolo 1H-benzodiazepin 5 one V, 7-methoxy-8(n-{4-[6-4 methyl hexahydro-1 prazinyl)-1H-benzo[d]imidazol-2-yl[phenoxy)alkyl)oxy-(11aS)-1,2,3-11a-tetrahydro-5H-pyrrolo[2,1-c)[1,4]benzodiazepin-5 one IX and 7-methoxy-8(n-{4-[6-4-ethylhexahydro-1-pyraziny)-1H-benzo[d]imidazol-2-yl]phenoxy}alkyl)-oxy-(11aS)-1,2,3,-11a-tetrahydro 5H-pyrrolo[2,1-c)[1,4]bebzidiazepin-5 one with aliphatic chain length variation of these compounds. These novel compounds also show DNA binding and anticancer (antitumour) activity. These novel pyrrolo[2,1-c][1,4] benzodiazepines have the general Formula XIV shown below:

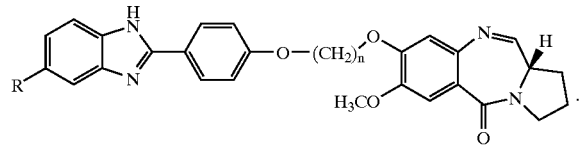

(XIV)

-continued

R = H, n = 3–5

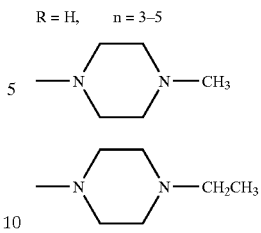

In a preferred embdodiment, present invention provides a process for the preparation of a novel pyrrolo[2,1-c][1,4] benzodiazepine hybrids selected from the compounds of formulae V, IX and XIII wherein R=H, N-methylpypazine, N-ethylpyperazine and "n" is 3 to 5.

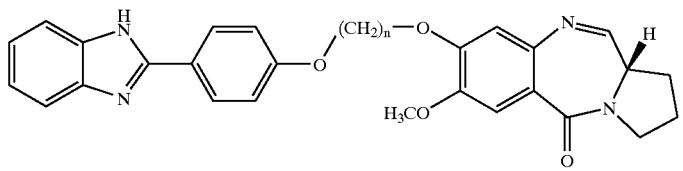

V n = 3–5

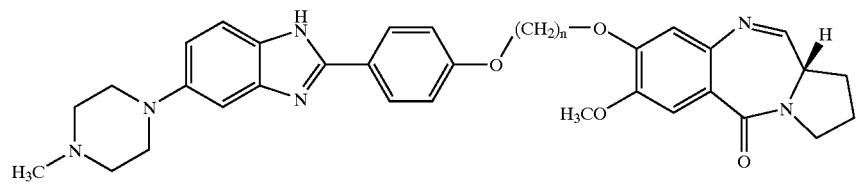

IX n = 3–5

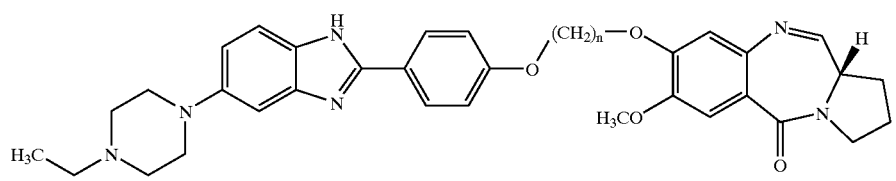

XIII n = 3–5

Accordingly the present process provides a process for preparation of pyrrolo[2,1-c]1,4]benzodiazepine hybrids of formula V

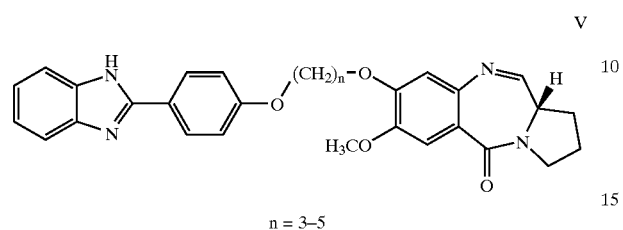

n = 3–5 which comprises reacting a 4-(1H-benzo[d]imidazol-2-yl) phenol of the formula I,

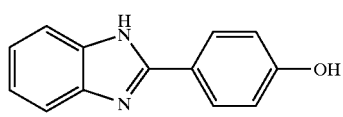

with N-[4-(n-bromoalkyloxy)-5-methoxyy-2-nitrobenzo-yl] pyrrolidine-2-carboxaldehyde diethyl thio acetal of formula II

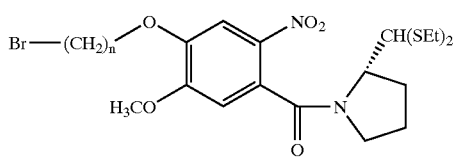

in the presence of K$_2$CO$_3$ in organic solvent for a period of 12 to 24 hrs, isolating (2S)-N-{4-(1H-benoz[d]imidazolo-2yl)phenoxy]alkyl-oxy-5methoxy-2-nitrobenzoyl}pyrrolidine-2-carboxaldehyde diethyl thioacetal III

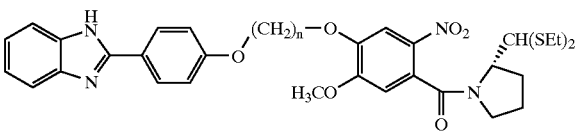

III

where "n" is 3 to 5, reducing said compound of formula III with SnCl$_2$. 2H$_2$O in the presence of organic solvent up to a reflux temperature, isolating the (2S)-N-{n-4-(1H-benzo [d]imidazolo-2yl)phenoxy]alkyl]-oxy-5-methoxy-2-aminobenzoyly}pyrrolidine-2-carboxaldehyde diethyl thio-acetal of the formula IV

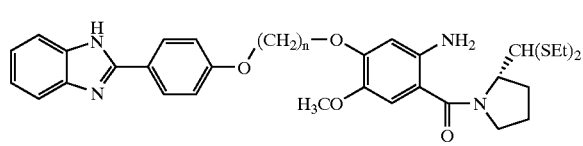

IV

where n is 3 to 5 by known methods, reacting the said amino compound of formula IV with conventional deprotecting agents in to produce pyrrolo[2,1-c]1,4]benzodiazepine hybrids of formula V, wherein "n" is as defined above.

In another embodiment, the present invention provides a process for preparation of pyrrolo[2,1-c]1,4]benzodiazepine hybrids of formula IX

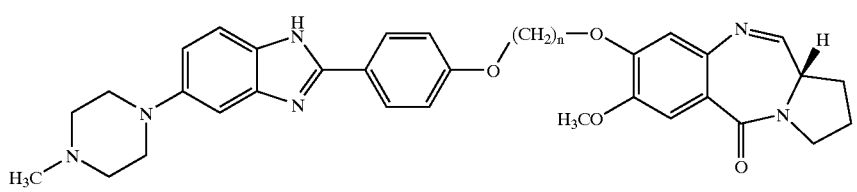

n = 3–5 which comprises reacting a 4-[6-4-methylhexahydro-1-pyrazinyl)-1H-benzo[imidazol-2-yl]phenol VI

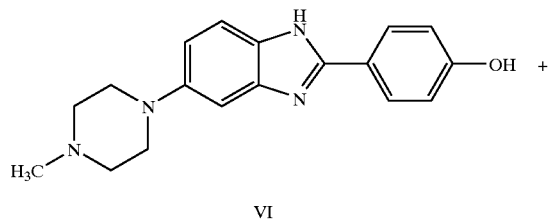

VI with N-[4-(n-bromoalkyloxy)-5-methoxy-2-nitrobenzo-yl] pyrrolidine-2-carboxaldehyde diethyl thio acetal of formula II

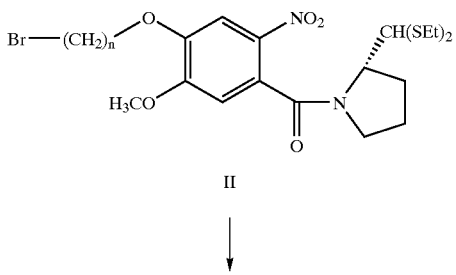

II in the presence of K$_2$CO$_3$ in organic solvent for a period of 12 to 24 hrs, isolating (2S)-N-{n-(4-[6-4-methylhexahydro-1-pyraxinyl)-1H-benzo[d]imidazol-2-yl]phenoxy]alkyl-oxy-5-methoxy-2-nitrobenzoy pyrrolidine-2-carboxaldehyde diethyl thioacetal VII

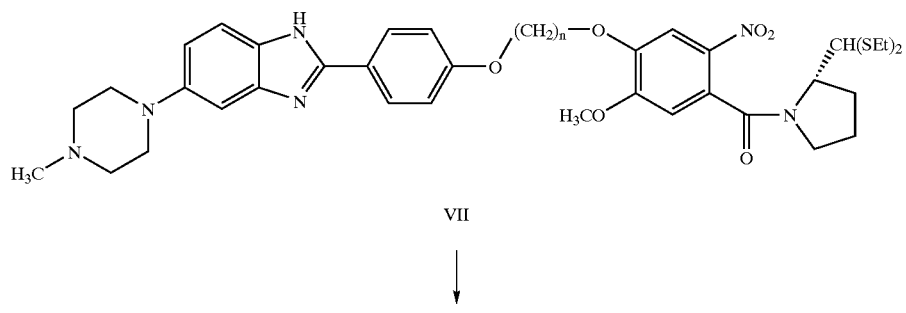

VII where "n" is 3 to 5, reducing said compound of formula VII with SnCl$_2$. 2H$_2$O in the presence of organic solvent up to a reflux temperature, isolating the (2S)-N-{n-(4-[6-(4-methylhexahydro-1-pyrazinyl)-1H-benzo[d]imidazol-2-yl]phenoxy]alkyl)-oxy-5-methoxy-2-aminobenzoy}pyrrolidine-2-carboxaldehyde diethyl thioacetal VIII

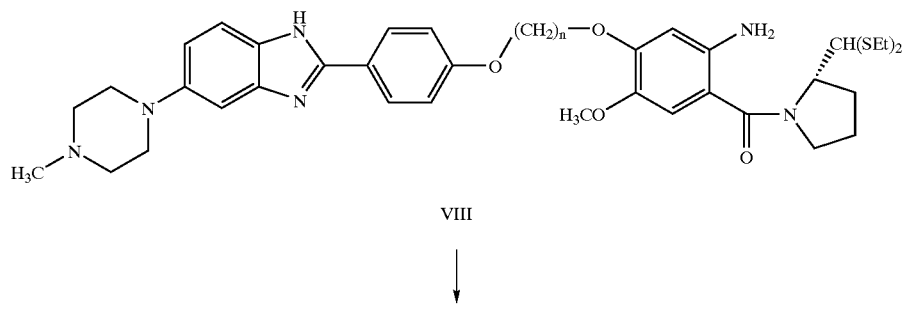

VIII and reacting the said amino compound of formula VIII with conventional deprotecting agents in to produce pyrrolo[2,1-c]1,4]benzodiazepine hybrids of formula IX wherein "n".

In yet another embodiment, the present invention provides a process for preparation of pyrrolo[2,1-c]1,4] benzodiazepine hybrids of formula XIII

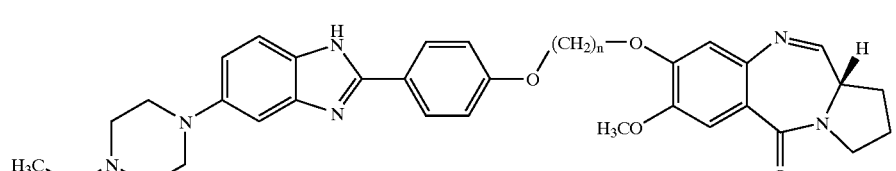

XIII n = 3–5 which comprises reacting a 4-[6-(4-ehtylhexahydro-I-pyrazinyl)-1H-benzo[d]imidazol-2-yl]phenol X

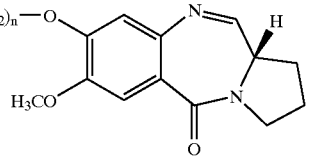

X with N-[4-(n-bromoalkyloxy)-5-methoxyy-2-nitrobenzo-yl] pyrrolidine-2-carboxaldehyde diethyl thio acetal of formula II

II in the presence of $K_2CO_3$ in organic solvent for a period of 12 to 24 hrs, isolating (2S)-N-{n-(4-[6-4-ehtyhexahydro-1-pyrazinyl)-H-benzo[d]imidazol-2-yl]phenoxy]alkyl1]-oxy-5-methoxy-2-nitrobenzoyl}pyrrolidine-2-carboxaldehyde diethyl thioacetal XI

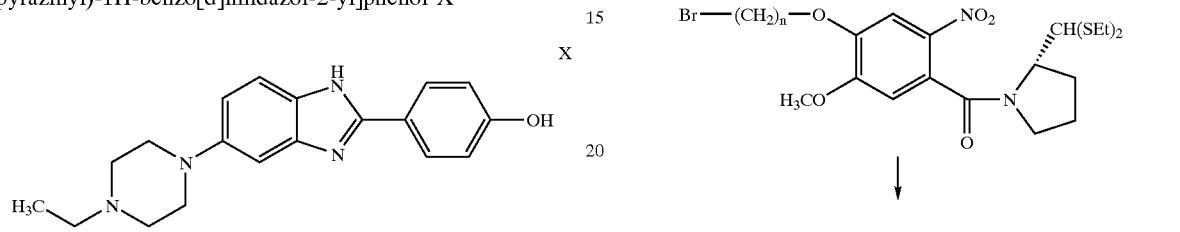

XI where "n" is 3 to 5, reducing said compound of formula XI with $SnCl_2 \cdot 2H_2O$ in the presence of organic solvent up to a reflux temperature, isolating (2S)-N-{n-(4-[6-(4-ehtylhexahydro-1-pyrazinyl)-1H-benzo[d]imidazol-2-yl] phenoxy]alkyl)-oxy-5-methoxy-2-aminobenzoyl}pyrrolidine-2-carboxaldehyde diethyl thioacetal XII where n is 3 to 5

XII

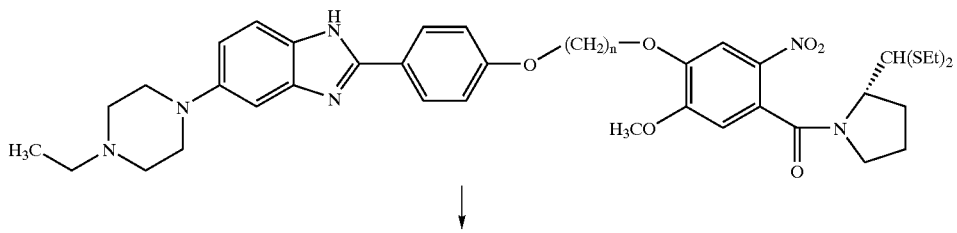

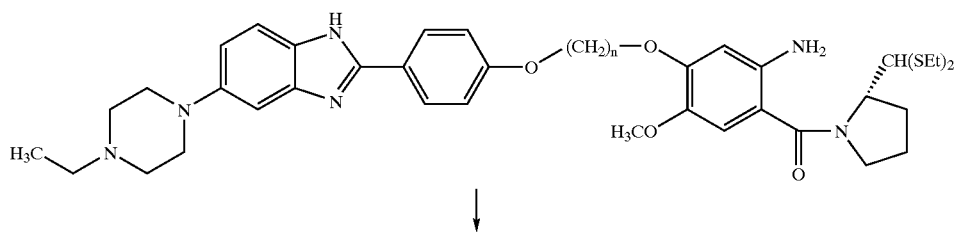

and reacting the said amino compound of formula XII with conventional deprotecting agents to produce pyrrolo[2,1-c] 1,4]benzodiazepine hybrids of formula XIII wherein "n" is as defined above.

DETAILED DESCRIPTION

The precursors, 4-(1H-benzo[d]imidazo 1-2-yl)phenol 1,4-[6-(4-methylhexadhyro-1-pyrazinyl)-1H-benzo[d] imidazo 1-2-yl]phenol VI and 4-[6-(4ehtylhexahydro-1-pyrazinyl)-1H-benzo[d]dimidazol-2-yl]phenol X (Ji, Yu,; Hasler, W,; Schmitt, V. R.; Dorn, A.; Baily C.; Waring, M. J.; Hochstrasser, R.; Keupin, W. Bioorg Med Chem Lett. 2001, 9, 2905) and (2S)-N-[4-(b-bromoalkyloxy)-5-methoxy-2-nitrobenzo-yl]pyrrolidine-2-carboxaldehyde diethyl thioacetal II (Kamal, A.; Ramesh, G.; Laxman, N.; Ramulu, P.; Srinivas, O,; Neelima, K.; Kondapi, A. K.; Srinu, V. B.; Nagarajaram H. M. J. Med. Chem. 2002, 45,4679) have been prepared by literature methods.

Some representative compound of formulae V/IX/XIII of present invention are given below 1. 7-Methoxy-8-n{3-[4-(1H-benzo[d]imidazolo-2-yl) phenoxyl]propoxy}-(11aS)1,2,3-11a-tetrahydro-5H-pyrrolo [2,1-c]01,4]benzodiazepin-5-one. 1
2. 7-Methoxy-8-{4-[4-)1H-benzo[d]imidazolo-2yl phenoxy]butoxy}-(11aS)1,2,3-11a-tetrahydro-5H-pyrrolo [2,1-c][1,4]benzodiazepin-5-one
3. 7-Methoxy-8-{5-[4-(1H-benzo[d]imidazolo-2yl) phenoyxl]pentyloxy}-(11aS)1,2,3,-11a-tetrahydro-5H-pyrrolo{2,1-c][1,4]benzodiazepin-5-one
4. 7-methoxy-8-(3-{4-[6-(4-methylhexahydro-1-pyrazinyl)-1H-benzol[d]imidazol-2-yl] phexnoxy}propoxy)-(11aS)-1,2,3-11a-tetrahydro-5H-pyrrolo[2,1-c]
5. 7-methoxy-8-(4-{4-[6-(4-methylhexaydro-1-pyrazinyl)-1H-benzol[d]imidazol-2-yl]phenoxy}butoxy)-(11aS)-1,2,3,-11a-tetrahydro-5H-pyrrolo [2,1-c][1,4] benzodiazepin-5-one
6. 7-methoxy-8-(5-{4-[6-(4-methylhexahydro-1-pyrazinyl)-1H-benzo[d]imidazol-2-yl]phenoxy}pentyloxy)-(11aS)-1,2,3-11a-tetrahydro-5-pyrrolo [2,1-c) [1,4] benzodiazepin-5-one
7. 7-methoxy-8-(3-{4-[6-(4-ethyexahydro-1-pyrazinyl)-1H-benzo[d]imidazol-2-yl]phenoxy)-(11aS)-1,2,3,-11a-tetrahydro-5H-pyrrolo[2,1-c][1,4]benzodiazepin-5-one
8. 7-methoxy-8-(4-{4-[6-(4-ethylhexahydro-1-pyrazinyl)-1H-benzo[d]imidazol-2-yl]phenoxy}butoxy-(11aS)-1,2,3-11a-tetrahydro-5H-pyrrolo [2,1-c][1,4] benzodiazepin-5-one
9. 7-methoxy-8-(5-{4-[6-(4-ethylhexahydro-1-pyrazinyl)-1H-benzo[d]imidazol-2-yl]phenoxy}pentyloxy-(11aS)-1,2,3-11a-tetrahydro-5H-pyrrolo[2,1-c][1,4] benzodiazepin-5-one These new analogues of pyrrolo[2,1-c][1,4] benzodiazepin hybrids linked at C-8 position have shown promising DNA binding activity in various cell lines. The molecules synthesized are of immense biological significance with potential sequence selective DNA-binding property. This resulted in design and synthesis of new congeners as illustrated in the following reaction Schemes which comprise:

1. The either linkage at C-8 position of DC-81 intermediates with substituted 2-phenoxy benzimadazole moiety.
2. Up to refluxing the reaction mixture for 12–48 h.
3. Synthesis of C-8 linked PBD antitumour antibiotic hybrid imines.
4. Purification by column chromatography using different solvents like ethyl acetate hexane, dichloromethane, chlorform and methanol.

Reaction Schemes

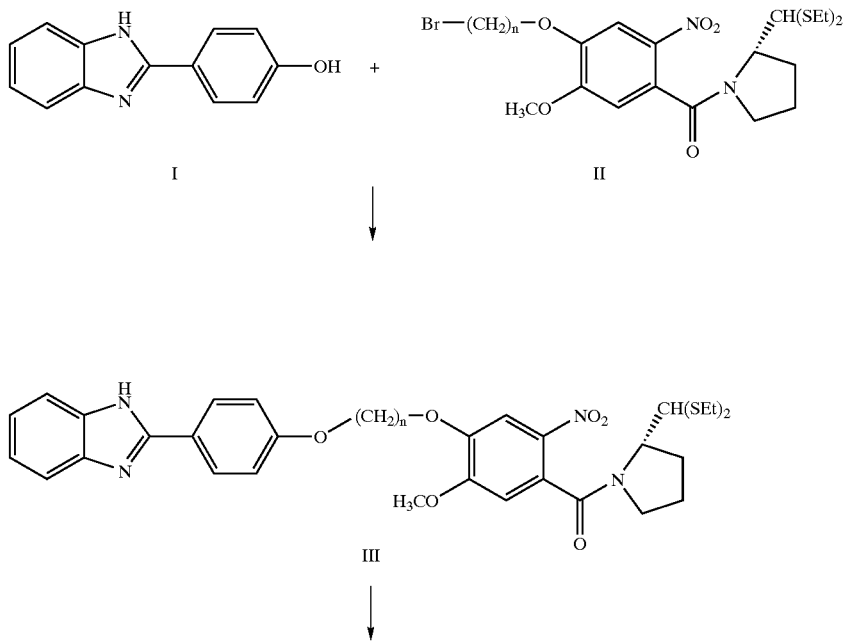

-continued
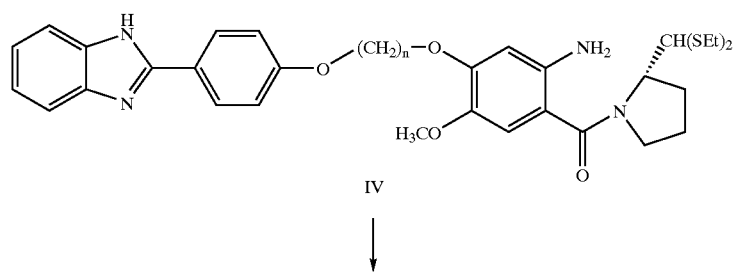
IV
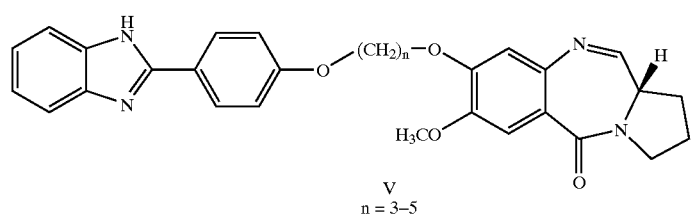
V
n = 3–5
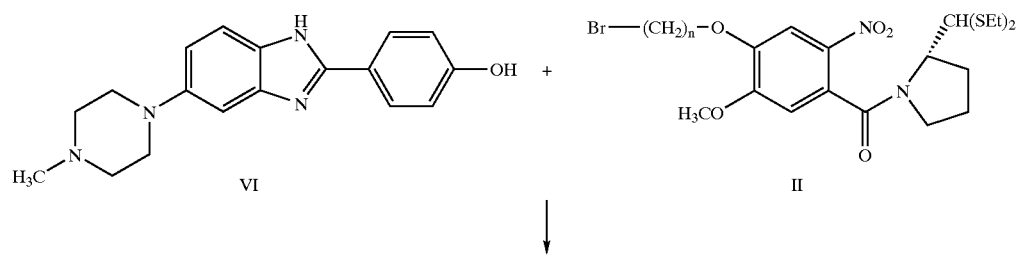
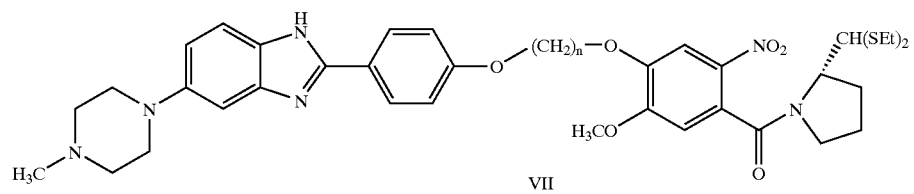
VII
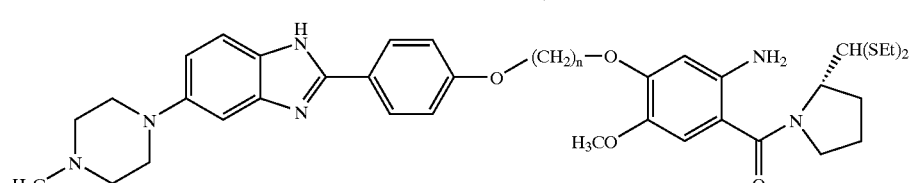
VIII
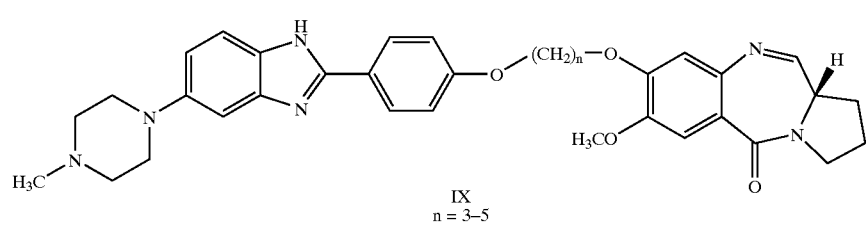
IX
n = 3–5

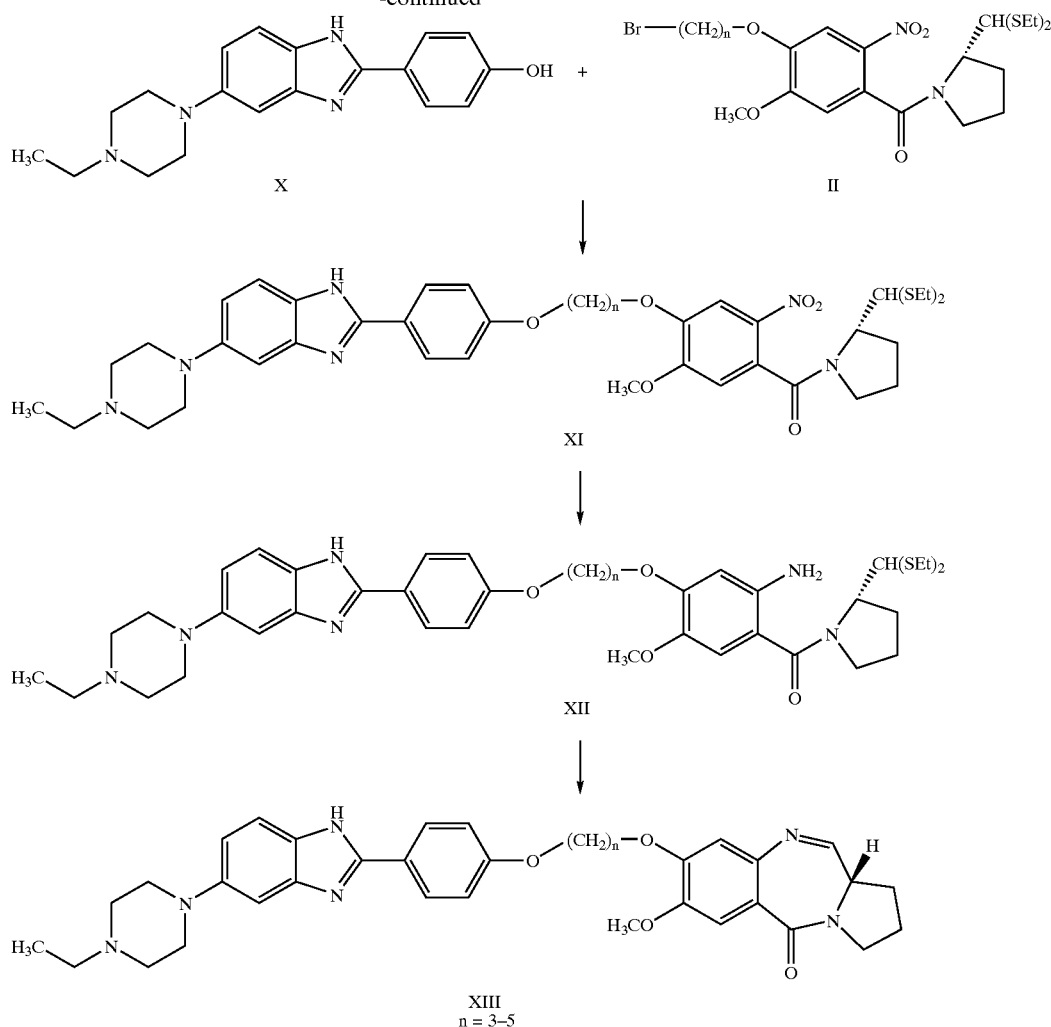

XIII
n = 3–5

The invention will now be described with reference to the following example, which are given by way of illustration and therefore should not be construed to the present limit of the scope of invention.

EXAMPLE 1

Compound 4-[1H-benzo[d]imidazol-2-yl]phenol I (210 mg, 1 mmol) and (2S)-N-4-(3-bromobutyloxy)-5-methoxy-2-nitrobenzoyl]pyrrolidin-2-carboxaldehyde diethyl thioacetal of formula II (521 mg, 1 mmol) was taken in dry DMF (10 mL). K2CO3 (690 mg, 5 mmol) was added and the mixture was stirred for 12 to 24 hrs. The reaction mixture was poured in to ice-water then solid was formed and it was filtered and aqueous media was extracted with EtOAc and CHCl₃ (50 mL), then the extracted solution was evaporated in vacuum to obtain the solid compound. Two solids were combined and the crude material was chromatographed over silica gel using chloroform/methanol (8:2) solvent to give compound (2S)-N-{3-(4-(1H-benzo[d]imidazol-2-yl]phenoxy)propoxy-5-method-2-nitrobenzoyl}pyrrolidine-2-carboxaldehyde diethyl thioacetal VII as a sticky solid.

The compound (2S)-N-{3-(4-(1H-benzo[d]imidazol-2-yl]phenoxy)propoxy-5-method-2-nitrobenzoyl}pyrrolidine-2-carboxaldehyde diethyl thioacetal III (0.649 mg, 1 mmol) was dissolved in methanol (15 ml) and added SnCl₂.2H₂O (1.13 g, 5 mmol) was refluxed fro 2–5 h or until the TLC indicated that reaction was completed. The reaction mixture was then adjusted to pH 8 carefully with saturated NaHCO₃ solution, diluted with ethyl acetate, filtered through celite and extracted. The combined organic phase was dried over Na₂SO₄, and evaporated under vacuum to afford the crude compound (2S)-N-{3-(4-(1H-benzo[d]imidazolo-2-yl]phenoxy)propoxy-5-method-2-aminobenzoyl}pyrrolidine-2-carboxaldehyde diethyl thioacetal VIII.

A solution of compound (2S)-N-(3-(4-(1H-benzo[d]imidazolo-2-yl]phenoxy)propoxy-5-method-2-aminobenzoyl}pyrrolidine-2-carboxaldehyde diethyl thioacetal IV (619 mg, 1 mmol), HgCl₂ (613 mg, 2.26 mmol) and CaCO3 (246 mg, 2.46 mmol) in MeCN-water (4:1) was stirred slowly at room temperature until TLC indicates completed loss of starting material. The reaction mixture was diluted with EtOAc (30 mL) and filtered through a celite bed. The clear brown organic supernatant was extracted with saturated 5% NaHCO₃ (20 mL), brine (20 mL) and the combined organic phase was dried (Na2SO₄). The organic layer was evaporated in vacuum and purified by column chromatography (95% CH₂Cl₂—MeOH) to give compound 7-methoxy-8-(3-[4-[1H-benzo[d]imidazol-2-yl]phenyl}protoxy)-(11aS)-1,2,3,-11a-tetrahydro-5H-pyrrolo[2,1-c][1,4]benzodiazepin-5-one.

$^1$H NMR (CDCl$_3$) & 1.90–2.10 (m, 2H), 2.20–2.39 (m, 4H), 3.90 (s, 3H), 3.90 (m, 3H), 4.10–4.30 (m, 4H), 6.80–6.98 (3s, 3H), 7.10–7.30 (m, 2H), 7.45 (s, 1H), 7.5–7.65 (m, 3H), 7.85–7.90 (d, 2H); MS (FAB) 497 [M+H]$^+$.

EXAMPLE 2

Compound 4-[1H-benzo[d]imidazol-2-yl]phenol I (210 mg, 5 mmol) and (2S)-N-[4-(4-bromobutyloxy)-5-methoxy-2-nitrobenzoyl]pyrrolidin-2-carboxaldehyde diethyl thioacetal of formula II (535 mg, 1 mmol) was taken in dry DMF (10 mL). K$_2$CO$_3$ (690 mg, 5 mmol) was added and the mixture was stirred for 12 to 24 hrs. The reaction mixture was poured in to ice-water then solid was formed and it was filtered and aqueous media was extracted with EtOAc and CHCl$_3$ (50 mL). Then the extracted solution was evaporated in vacuum to obtain the solid compound. Two solids were combined and the crude material was chromatographed over silica gel using chloroform/methanol (8:2) solvent to give compound (2S)-N-{3-(4-(1H-benzo[d]imidazol-2-yl]phenoxy)propoxy]butoxy-5-method-2-nitrobenzoyl}pyrrolidine-2-carboxaldehyde diethyl thioacetal III as a sticky solid.

The compound (2S)-N-{4-(4-(1H-benzo[d]imidazol-2-yl]phenoxy)-5-methoxy-2-nitrobenzoyl}pyrrolidine-2-carboxaldehyde diethyl thioacetal III (633 mg, 1 mmol) was dissolved in methanol (15 ml) and added with SnCl$_2$.2H$_2$O (1.12 g, 5 mmol) and was refluxed for 2–5 h or until the TLC indicated that reaction was completed. The reaction mixture was then adjusted to pH 8 carefully with saturated NaHCO$_3$ solution, diluted with ethyl acetate, filtered through celite and extracted. The combined organic phase was dried over Na$_2$SO$_4$, and evaporated under vacuum to afford the crude compound (2S)-N-(3-(4-(1H-benzo[d]imidazolo-2-yl]phenoxy]butoxy-5-methoxy-2-aminobenzoyl}pyrrolidine-2-carboxaldehyde diethyl thioacetal IV.

A solution of compound (2S)-N-{4-(4-(1H-benzo[d]imidazolo-2-yl]phenoxy)butoxy-5-method-2-aminobenzoyl}pyrrolidine-2-carboxaldehyde diethyl thioacetal IV (603 mg, 1 mmol), HgCl$_2$ (613 mg, 2.26 mmol) and CaCO$_3$ (246 mg, 2.46 mmol) in MeCN-water (4:1) was stirred slowly at room temperature until TLC indicates completed loss of starting material. The reaction mixture was diluted with EtOAc (30 mL) and filtered through a celite bed. The clear brown organic supernatant was extracted with saturated 5% NaHCO$_3$ (20 mL), brine (20 mL) and the combined organic phase was dried (Na$_2$SO$_4$). The organic layer was evaporated in vacuum and purified by column chromatography (95% CH$_2$Cl$_2$—MeOH) to give compound 7-methoxy-8(3-[4-[1H-benzo[d]imidazol-2-yl]phenoxy}butoxy)-(11aS)-1,2,3,-11a-tetrahydro-5H-pyrrolo[2,1-c][1,4]benzodiazepin-5-one
$^1$H NMR (CDCl$_3$) & 1.80–2.20 (m, 6H), 2.21–2.42 (m, 2H), 3.50–3.95 (m, 6H), 4.05–4.30 (m, 4H), 6.70–682 (m, 3H), 7.19–7.21 (m, 2H), 7.3 (s, 1H), 7.59–7.70 (m, 3H), 7.80–7.70 (m, 3H), 7.80–7.90 (d, 2H); MS (FAB) 511[M+H]$^+$.

EXAMPLE 3

Compound 4-[1H-benzo[d]imidazol-2-yl]phenol I (210 mg, 1 mmol) and (2S)-N-[4-(5-bromobutyloxy)-5-methoxy-2-nitrobenzoyl]pyrrolidin-2-carboxaldehyde diethyl thioacetal of formula II (549 mg, 5 mmol) was taken in dry DMF (10 mL), K$_2$CO$_3$ (690 mg, 5 mmol) was added and the mixture was stirred for 12–24$^{th}$. The reaction mixture was poured in to ice-water then solid was formed and it was filtered and aqueous media was extracted with EtOAc and CHCl$_3$ (50 mL). Then the extracted solution was evaporated in vacuum to obtain the solid compound. Two solids were combined and the crude material was chromatographed over silica gel using chloroform/methanol (9:1) solvent to give compound (2S)-N-{5-(4-(1H-benzo-[d]imidazol-2-yl]phenoxy)pentyloxy-5-method-2-nitrobenzoyl}pyrrolidine-2-carboxaldehyde diethyl thioacetal III as a sticky solid.

The compound (2S)-N-{5-(4-(1H-benzo[d]imidazol-2-yl]phenoxy)pentyloxy-5-methoxy-2-nitrobenzoyl}pyrrolidine-2-carboxaldehyde diethyl thioacetal III (0.647 g, 1 mmol) was dissolved in methanol (15 ml) and added with SnCl$_2$.2H$_2$O (1.12 g, 5 mmol) was refluxed fro 2–5 h or until the TLC indicated that reaction was completed. The reaction mixture was then adjusted to pH 8 carefully with saturated NaHCO$_3$ solution, diluted with ethyl acetate, filtered through celite and extracted. The combined organic phase was dried over Na$_2$SO$_4$, and evaporated under vacuum to afford the crude compound (2S)-N-{5-(4-(1H-benzo[d]imidazolo-2-yl]phenoxy]pentyloxy-5-methoxy-2-aminobenzoyl}pyrrolidine-2-carboxaldehyde diethyl thioacetal IV.

A solution of compound (2S)-N-{5-(4-(1H-benzo[d]imidazolo-2-yl]phenoxy)pentyloxy-5-method-2-aminobenzoyl}pyrrolidine-2-carboxaldehyde diethyl thioacetal III (617 mg, 1 mmol), HgCl$_2$ (613 mg, 2.26 mmol) and CaCO$_3$ (246 mg, 2.46 mmol) in MeCN-water (4:1) was stirred slowly at room temperature until TLC indicates completed loss of starting material. The reaction mixture was diluted with EtOAc (30 mL) and filtered through a celite bed. The clear brown organic supernatant was extracted with saturated 5% NaHCO$_3$ (20 mL), brine (20 mL) and the combined organic phase was dried (Na$_2$SO$_4$). The organic layer was evaporated in vacuum and purified by column chromatography (95% CH$_2$Cl$_2$—MeOH) to give compound 7-methoxy-8-(5-[4-[1H-benzo[d]imidazol-2-yl]phenoxy}pentyloxy)-(11aS)-1,2,3,-11a-tetrahydro-5H-pyrrolo[2,1-c][1,4]benzodiazepin-5-one.
$^1$H NMR (CDCl$_3$) & 1.60–2.19 (m, 8H), 2.25–2.39 (m, 2H), 3.60–4.20 (m, 10H), 6.70–6.90 (m, 3H), 7.19–7.30 (m, 2H), 7.50 (s, 1H), 7.65–7.78 (m, 3H), 7.90–8.01 (d, 2H); MS (FAB) 525[M+H]$^+$.

EXAMPLE 4

Compound 4-[6-(4-methylhexahydro-1-pyrazinyl)-1H-benzo[d]imidazol-2-yl]phenol VI (328 mg, 1 mmol) and (2S)-N-[4-(3-bromobutyloxy)-5-methoxy-2-nitrobenzoyl]pyrrolidin-2-carboxaldehyde diethyl thioacetal of formula II (521 mg, 1 mmol) was taken in dry DMF (10 mL). K$_2$CO$_3$ (690 mg, 5 mmol) was added and the mixture was stirred for 12–24$^{th}$. The reaction mixture was poured in to ice-water then solid was formed and it was filtered and aqueous media was extracted with EtOAc and CHCl$_3$ (50 mL), then the extracted solution was evaporated in vacuum to obtain the solid compound. Two solids were combined and the crude material was chromatographed over silica gel using chloroform/methanol (9:1) solvent to give compound (2S)-N-{3-(4-(6(4-Methylhexahydro-1-pyrazinyl)-1H-benzo[d]imidazol-2-yl]phenoxy)propoxy-5-methoxy-2-nitrobenzoyl}pyrrolidine-2-carboxaldehyde diethyl thioacetal VII as a sticky solid.

The compound (2S)-N-{3-(4-[6-(4-methylhexahydro-1-pyrazinyl)-1H-benzo[d]imidazol-2-yl]phenoxy)propoxy-5-methoxy-2-nitrobenzoyl1}pyrrolidine-2-carboxaldehyde diethyl thioacetal VII (0.767 g, 1 mmol) was dissolved in methanol (15 ml) and added with SnCl$_2$.2H$_2$O (1.12 g, 5 mmol) was refluxed fro 5–7 h or until the TLC indicated that reaction was completed. The reaction mixture was then adjusted to pH 8 carefully with saturated NaHCO₃ solution, diluted with ethyl acetate, filtered through celite and extracted. The combined organic phase was dried over Na₂SO₄, and evaporated under vacuum to afford the crude compound (2S)-N-(3-(4-[6-(4-methylhexahydro-1-pyrazinyl)-1H-benzo[d]imidazol-2-yl]imidazol-2-yl]phenoxy)propoxy-5-methoxy-2-aminobenzoyl}pyrrolidine-2-carboxaldehyde diethyl thioacetal VIII.

A solution of compound (2S)-N-{3-(4-[6-(4-methylhexahydro-1-pyrazinyl)-1H-benzo[d]imidazol-2-yl]imidazol-2-yl]phenoxy)propoxy-5-methoxy-2-aminobenzoyl}pyrrolidine-2-carboxaldehyde diethyl thioacetal VIII (637 mg, 1 mmol), HgCl₂ (613 mg, 2.26 mmol) and CaCO3 (246 mg, 2.46 mmol) in MeCN-water (4:1) was stirred slowly at room temperature until TLC indicates completed loss of starting material. The reaction mixture was diluted with EtOAc (30 mL) and filtered through a celite bed. The clear brown organic supernatant was extracted with saturated 5% NaHCO₃ (20 mL), brine (20 mL) and the combined organic phase was dried (Na2SO4). The organic layer was evaporated in vacuum and purified by column chromatography (80% CH2Cl2—MeOH) to give compound 7-methoxy-8(3-[4-[6-(4-methylhexahydro-1-pyrazinyl)-1H-benzo[d]imidazol-2-yl]phenoxy}propoxy)-(11aS)-1,2,3,-11a-tetrahydro-5H-pyrrolo[2,1-c][1,4]benzodiazepin-5-one.
¹H NMR (CDCl₃) & 1.90–2.15 (m, 3H), 2.20–2.30 (m, 3H), 2.40 (s, 3H), 2.60–2.75 (m, 4H), 3.10–3.20 (m, 3H), 3.90 (s, 3H), 4.10–4.35 (m, 4H), 6.75 (s, 1H), 6.80–7.1 (m, 5H), 7.60–7.70 (d, 1H, J=4.4 Hz), 7.90–8.10 (d, 2H): MS (FAB) 595 [M+H]⁺.

EXAMPLE 5

Compound 4-[6-(4-methylhexahydro-1-pyrazonyl)-1H-zenzo[d]imidazol-2-yl]phenol VI (328 g, 1 mmol) and (2S)-N-4-(4-bromobutyloxy)-5-methoxy-2-nitrobenzoyl]pyrrolidin-2-carboxaldehyde diethyl thioacetal of formula II (535 mg, 1 mmol) was stirred for 12–24$^{th}$. The reaction mixture was poured in to ice-water then solid was formed and it was filtered and aqueous media was extracted with EtOAc and CHCl3 (50 mL), then the extracted solution was evaporated in vacuum to obtain the solid compound. Two solids were combined and the crude material was. Chromatographed over silica gel using chloroform/methanol (8:2) solvent to give compound (2S)-N-{4-(4-[6-(4-methylhexahydro-1-pyrazinyl)-1H-benzo[d]imidazol-2-yl]phenoxy)butoxy-5-method-2-nitrobenzoyl}pyrrolidine-2-carboxaldehyde diethyl thioacetal VII as a sticky solid.

The compound (2S)-N-{4-(4-[6-(4-methylhexahydro-1-pyrazinyl)1H-benzo[d]imidazol-2-yl]phenoxy)propoxy-5-methoxy-2-nitrobenzoyl1}pyrrolidine-2-carboxaldehyde diethyl thioacetal VII (0.781 g, 1 mmol) was dissolved in methanol (15 ml) and added with SnCl₂.2H₂O (1.12 g, 5 mmol) was refluxed fro 5–7 h or until the TLC indicated that reaction was completed. The reaction mixture was then adjusted to pH 8 carefully with saturated NaHCO₃ solution, diluted with ethyl acetate, filtered through celite and extracted. The combined organic phase was dried over Na₂SO₄, and evaporated under vacuum to afford the crude compound (2S)-N-{4-(4-[6-(4-methylhexahydro-1-pyrazinyl)-1H-benzo[d]imidazol-2-yl]imidazol-2-yl]phenoxy)propoxy-5-methoxy-2-aminobenzoyl}pyrrolidine-2-carboxaldehyde diethyl thioacetal VIII.

A solution of compound (2S)-N-{4-(4-[6-(4-methylhexahydro-1-pyrazinyl)-1H-benzo[d]imidazolo-2-yl]imidazol-2-yl]phenoxy)propoxy-5-methoxy-2-aminobenzoyl}pyrrolidine-2-carboxaldehyde diethyl thioacetal VIII (751 mg, 1 mmol), HgCl₂ (613-mg, 2.26 mmol) and CaCO3 (246 mg, 2.46 mmol) in MeCN-water (4:1) was stirred slowly at room temperature until TLC indicates completed loss of starting material. The reaction mixture was diluted with EtOAc (30 mL) and filtered through a celite bed. The clear brown organic supernatant was extracted with saturated 5% NaHCO₃ (20 mL), brine (20 mL) and the combined organic phase was dried (Na2SO₄). The organic layer was evaporated in vacuum and purified by column chromatography (80% CH₂Cl₂—MeOH) to give compound 7-methoxy-8(4-[4-[6-(4-methylhexahydro-1-pyraziny)-1H-benzo[d]imidazol-2-yl]phenoxy}butoxy)-(11aS)-1,2,3,-11a-tetrahydro-5H-pyrrolo[2,1-c][1,4]benzodiazepin-5-one.
¹H NMR (CDCl₃) & 1.80–2.18 (m, 3H), 2.35 (m, 3H), 2.60–2.70 (s, 4H), 3.10–3.20 (m, 4H), 3.60–3.80 (m, 3H), 3.90 (s, 3H), 4.01–4.25 (m, 4H), 6.72 (s, 1H), 7.35 (m, 5H), 7.61–7.30 (d, 1H. J=3.6 Hz), 7.98–8.03 (d, 2H): MS (FAB) 6.9 [M+H]⁺.

EXAMPLE 6

Compound 4-[6-(4-methylhexahydro-1-pyrazonyl)-1H-zenzo[d]imidazol-2-yl]phenol VI (328 g, 5 mmol) and (2S)-N-4-(5-bromobutyloxy)-5-methoxy-2-nitrobenzoyl]pyrrolidin-2-carboxaldehyde diethyl thioacetal of formula II (549 mg, 1 mmol) was taken in dry DMF (10 mL). K2CO3 (690 mg, 5 mmol) was added and the mixture was stirred for 12–24$^{th}$. The reaction mixture was poured in to ice-water then solid was formed and it was filtered and aqueous media was extracted with EtOAc and CHCl3 (50 mL), then the extracted solution was evaporated in vacuum to obtain the solid compound. Two solids were combined and the crude material was. Chromatographed over silica gel using chloroform/methanol (8:2) solvent to give compound (2S)-N-{5-(4-[6-(4-methylhexahydro-1-pyrazinyl)-1H-benzo[d]imidazol-2-yl]phenoxy)pentyloxy-5-method-2-nitrobenzoyl}pyrrolidine-2-carboxaldehyde diethyl thioacetal VII as a sticky solid.

The compound (2S)-N-{5-(4-[6-(4-methylhexahydro-1-pyrazinyl)-1H-benzo[d]imidazol-2-yl]phenoxy)propoxy-5-methoxy-2-nitrobenzoyl1}pyrrolidine-2-carboxaldehyde diethyl thioacetal VII (0.795 g, 1 mmol) was dissolved in methanol (15 ml) and added with SnCl₂.2H₂O (1.12 g, 5 mmol) was refluxed fro 5–7 h or until the TLC indicated that reaction was completed. The reaction mixture was then adjusted to pH 8 carefully with saturated NaHCO₃ solution, diluted with ethyl acetate, filtered through celite and extracted. The combined organic phase was dried over Na₂SO₄, and evaporated under vacuum to afford the crude compound (2S)-N-{5-(4-[6-(4-methylhexahydro-1-pyrazinyl)-1H-benzo[d]imidazol-2-yl]imidazol-2-yl]phenoxy)pentyloxy-5-methoxy-2-aminobenzoyl}pyrrolidine-2-carboxaldehyde diethyl thioacetal VIII.

A solution of compound (2S)-N-{4-(5-[6-(4-methylhexahydro-1-pyrazinyl)-1H-benzo[d]imidazolo-2-yl]imidazol-2-yl]phenoxy)propoxy-5-methoxy-2-aminobenzoyl}pyrrolidine-2-carboxaldehyde diethyl thioacetal (765 mg, 1 mmol), HgCl₂ (613 mg, 2.26 mmol) and CaCO₃ (246 mg, 2.46 mmol) in MeCN-water (4:1) was stirred slowly at room temperature until TLC indicates completed loss of starting material. The reaction mixture was diluted with EtOAc (30 mL) and filtered through a celite bed. The clear brown organic supernatant was extracted with saturated 5% NaHCO₃ (20 mL), brine (20 mL) and the combined organic phase was dried (Na2SO₄). The organic layer was evaporated in vacuum and purified by column chromatography (80% CH₂Cl₂—MeOH) to give compound 7-methoxy-8(5-[4-[6-(4-methylhexahydro-1-pyraziny)-1H-benzo[d]imidazol-2-yl]phenoxy}butoxy)-(11aS)-1,2,3,-11a-tetrahydro-5H-pyrrolo[2,1-c][1,4]benzodiazepin-5-one.

¹H NMR (CDCl₃) & 1.75–2.95 (m, 3H), 2.19–2.21 (m, 3H), 2.55–2.61 (m, 4H), 3.10–3.20 (m, 4H), 3.60–3.80 (m, 3H), 3.85 (s, 3H), 3.90–4.19 (m, 4H), 6.68 (s, 1H), 6.78–6.90 (m, 4H), 6.90 (s, 1H) 7.50–7.60 (d, 1H, J=4.4 Hz), 7.90–8.09 (d, 2H): MS (FAB) 623 [M+H]⁺.

EXAMPLE 7

Compound 4-[6-(4-methylhexahydro-1-pyrazonyl)-1H-zenzo[d]imidazol-2-yl]phenol X (342 g, 5 mmol) and (2S)-N-4-(3-bromobutyloxy)-5-methoxy-2-nitrobenzoyl] pyrrolidin-2-carboxaldehyde diethyl thioacetal of formula II (521 mg, 1 mmol) was taken in dry DMF (10 mL). K₂CO₃ (690 mg, 5 mmol) was added and the mixture was stirred for 12–24$^{th}$. The reaction mixture was poured in to ice-water then solid was formed and it was filtered and aqueous media was extracted with EtOAc and CHCl3 (50 mL), then the extracted solution was evaporated in vacuum to obtain the solid compound. Two solids were combined and the crude material was. Chromatographed over silica gel using chloroform/methanol (8:2) solvent to give compound (2S)-N-{3-(4-[6-(4-methylhexahydro-1-pyrazinyl)-1H-benzo[d] imidazol-2-yl]phenoxy)propoxy-5-method-2-nitrobenzoyl}pyrrolidine-2-carboxaldehyde diethyl thioacetal VII as a sticky solid.

The compound (2S)-N-{3-(4-[6-(4-methylhexahydro-1-pyrazinyl)-1H-benzo[d]imidazol-2-yl]phenoxy)propoxy-5-methoxy-2-nitrobenzoyl1}pyrrolidine-2-carboxaldehyde diethyl thioacetal XI (0.781 g, 1 mmol) was dissolved in methanol (15 ml) and added with SnCl₂.2H₂O (1.12 g, 5 mmol) was refluxed fro 2–5 h or until the TLC indicated that reaction was completed. The reaction mixture was then adjusted to pH 8 carefully with saturated NaHCO₃ solution, diluted with ethyl acetate, filtered through celite and extracted. The combined organic phase was dried over Na₂SO₄, and evaporated under vacuum to afford the crude compound (2S)-N-{3-(4-[6-(4-methylhexahydro-1-pyrazinyl)-1H-benzo[d]imidazol-2-yl]imidazol-2-yl] phenoxy)propoxy-5-methoxy-2-aminobenzoyl}pyrrolidine-2-carboxaldehyde diethyl thioacetal XII.

A solution of compound (2S)-N-{3-(4-[6-(4-methylhexahydro-1-pyrazinyl)-1H-benzo[d]imidazolo-2-yl] imidazol-2-yl]phenoxy)propoxy-5-methoxy-2-aminobenzoyl}pyrrolidine-2-carboxaldehyde diethyl thioacetal (765 mg, 1 mmol), HgCl₂ (613 mg, 2.26 mmol) and CaCO₃ (246 mg, 2.46 mmol) in MeCN-water (4:1) was stirred slowly at room temperature until TLC indicates completed loss of starting material. The reaction mixture was diluted with EtOAc (30 mL) and filtered through a celite bed. The clear brown organic supernatant was extracted with saturated 5% NaHCO₃ (20 mL), brine (20 mL) and the combined organic phase was dried (Na₂SO₄). The organic layer was evaporated in vacuum and purified by column chromatography (80% CH₂Cl₂—MeOH) to give compound 7-methoxy-8-(3-[4-[6-(4-methylhexahydro-1-pyraziny)-1H-benzo[d]imidazol-2-yl]phenoxy}butoxy)-(11aS)-1,2,3,-11a-tetrahydro-5H-pyrrolo[2,1-c][1,4]benzodiazepin-5-one.

EXAMPLE 8

Compound 4-[6-(4-methylhexahydro-1-pyrazonyl)-1H-zenzo[d]imidazol-2-yl]phenol X (342 g, 5 mmol) and (2S)-N-4-(4-bromobutyloxy)-5-methoxy-2-nitrobenzoyl] pyrrolidin-2-carboxaldehyde diethyl thioacetal of formula II (535 mg, 1 mmol) was taken in dry DMF (10 mL). K₂CO₃ (690 mg, 5 mmol) was added and the mixture was stirred for 12–24$^{th}$. The reaction mixture was poured in to ice-water then solid was formed and it was filtered and aqueous media was extracted with EtOAc and CHCl₃ (50 mL), then the extracted solution was evaporated in vacuum to obtain the solid compound. Two solids were combined and the crude material was chromatographed over silica gel using chloroform/methanol (8:2) solvent to give compound (2S)-N-{4-(4-[6-(4-methylhexahydro-1-pyrazinyl)-1H-benzo[d] imidazol-2-yl]phenoxy)butoxy-5-method-2-nitrobenzoyl}pyrrolidine-2-carboxaldehyde diethyl thioacetal XI as a sticky solid.

The compound (2S)-N-{4(4-[6-(4-methylhexahydro-1-pyrazinyl)-1H-benzo[d]imidazol-2-yl]phenoxy)propoxy-5-methoxy-2-nitrobenzoyl1}pyrrolidine-2-carboxaldehyde diethyl thioacetal XI (0.795 g, 1 mmol) was dissolved in methanol (15 ml) and added with SnCl₂.2H₂O (1.12 g, 5 mmol) was refluxed fro 2–5 h or until the TLC indicated that reaction was completed. The reaction mixture was then adjusted to pH 8 carefully with saturated NaHCO₃ solution, diluted with ethyl acetate, filtered through celite and extracted. The combined organic phase was dried over Na₂SO₄, and evaporated under vacuum to afford the crude compound (2S)-N-{4-(4-[6-(4-methylhexahydro-1-pyrazinyl)-1H-benzo[d]imidazol-2-yl]phenoxy)butoxy-5-methoxy-2-aminobenzoyl}pyrrolidine-2-carboxaldehyde diethyl thioacetal XII.

A solution of compound (2S)-N-{4-(4-[6-(4-methylhexahydro-1-pyrazinyl)-1H-benzo[d]imidazol-2-yl] imidazol-2-yl]phenoxy)propoxy-5-methoxy-2-aminobenzoyl}pyrrolidine-2-carboxaldehyde diethyl thioacetal (765 mg, 1 mmol), HgCl₂ (613 mg, 2.26 mmol) and CaCO₃ (246 mg, 2.46 mmol) in MeCN-water (4:1) was stirred slowly at room temperature until TLC indicates completed loss of starting material. The reaction mixture was diluted with EtOAc (30 mL) and filtered through a celite bed. The clear brown organic supernatant was extracted with saturated 5% NaHCO₃ (20 mL), brine (20 mL) and the combined organic phase was dried (Na₂SO₄). The organic layer was evaporated in vacuum and purified by column chromatography (80% CH₂Cl₂—MeOH) to give compound 7-methoxy-8-(4-[4-[6-(4-methylhexahydro-1-pyraziny)-1H-benzo[d]imidazol-2-yl]phenoxy}butoxy)-(11aS)-1,2,3,-11a-tetrahydro-5H-pyrrolo[2,1-c][1,4]benzodiazepin-5-one.

EXAMPLE 9

Compound 4-[6-(4-methylhexahydro-1-pyrazonyl)-1H-zenzo[d]imidazol-2-yl]phenol X (342 g, 1 mmol) and (2S)-N-4-(5-bromobutyloxy)-5-methoxy-2-nitrobenzoyl]

pyrrolidin-2-carboxaldehyde diethyl thioacetal of formula II (549 mg, 5 mmol) was taken in dry DMF (10 mL). K$_2$CO$_3$ (690 mg, 5 mmol) was added and the mixture was stirred for 12–24$^{th}$. The reaction mixture was poured in to ice-water then solid was formed and it was filtered and aqueous media was extracted with EtOAc and CHCl$_3$ (50 mL), then the extracted solution was evaporated in vacuum to obtain the solid compound. Two solids were combined and the crude material was chromatographed over silica gel using chloroform/methanol (8:2) solvent to give compound (2S)-N-{3-(4-[6-(4-methylhexahydro-1-pyrazinyl)-1H-benzo[d]imidazol-2-yl]phenoxy)pentyloxy-5-method-2-nitrobenzoyl}pyrrolidine-2-carboxaldehyde diethyl thioacetal XI as a sticky solid.

The compound (2S)-N-{5(4-[6-(4-methylhexahydro-1-pyrazinyl)-1H-benzo[d]imidazol-2-yl]phenoxy)pentyloxy-5-methoxy-2-nitrobenzoyl1}pyrrolidine-2-carboxaldehyde diethyl thioacetal XI (0.809 g, 1 mmol) was dissolved in methanol (15 ml) and added with SnCl$_2$.2H$_2$O (1.12 g, 5 mmol) was refluxed fro 2–5 h or until the TLC indicated that reaction was completed. The reaction mixture was then adjusted to pH 8 carefully with saturated NaHCO$_3$ solution, diluted with ethyl acetate, filtered through celite and extracted. The combined organic phase was dried over Na$_2$SO$_4$, and evaporated under vacuum to afford the crude compound (2S)-N-{5-(4-[6-(4-etyylhexahydro-1-pyrazinyl)-1H-benzo[d]imidazol-2-yl]imidazol-2-yl]phenoxy)pentyloxy-5-methoxy-2-aminobenzoyl}pyrrolidine-2-carboxaldehyde diethyl thioacetal XII.

A solution of compound (2S)-N-{5-(4-[6-(4-ethylhexahydro-1-pyrazinyl)-1H-benzo[d]imidazol-2-yl]pentyloxy-5-methoxy-2-aminobenzoyl}pyrrolidine-2-carboxaldehyde diethyl thioacetal XII (779 mg, 1 mmol), HgCl$_2$ (613 mg, 2.26 mmol) and CaCO$_3$ (246 mg, 2.46 mmol) in MeCN-water (4:1) was stirred slowly at room temperature until TLC indicates completed loss of starting material. The reaction mixture was diluted with EtOAc (30 mL) and filtered through a celite bed. The clear brown organic supernatant was extracted with saturated 5% NaHCO$_3$ (20 mL), brine (20 mL) and the combined organic phase was dried (Na$_2$SO$_4$). The organic layer was evaporated in vacuum and purified by column chromatography (80% CH$_2$Cl$_2$—MeOH) to give compound 7-methoxy-8-(5-[4-[6-(4-ethylhexahydro-1-pyraziny)-1H-benzo[d]imidazol-2-yl]phenoxy}pentyloxy)-(11aS)-1,2,3,-11a-tetrahydro-5H-pyrrolo[2,1-c][1,4]benzodiazepin-5-one.

Biological activity: in vitro biological activity studies were carried out at National Cancer Institute (USA).

Cytotoxicity: Compound IX was evaluated for the primary anti-cancer activity (Table-1) and in vitro against sixty human tumour cells derived from nine cancer types (leukemia, non-small-cell lung, colon, CNS, melanoma, ovarian, prostate, and breast cancer). For each compound, dose response curves for each cell line were measured at a minimum of five concentrations at 20 fold dilutions. A protocol of 48 h continuous drug exposure was used and a sulforhodamine B (SRB) protein assay was used to estimate cell viability or growth. The concentration causing 50% cell growth inhibition (GI50), total cell growth control was calculated. The mean graph midpoint values of log10 TGI and log10 LC50 as well as log 10 GI50 for VI are listed in Table 2. As demonstrated by mean graph pattern, compound IV exhibits an interesting profile of activity and selectivity for various cell lines. The mean graph mid point of log10 TGI and log10 LC50 showed similar pattern to the log 10 GI 50 mean graph mid points.

TABLE 1 in vitro one dose primary anticancer assay[a], of PBD hybrid formula IX as representative compound.

| | Growth Percentages. | | |
|---|---|---|---|
| PBD hybrid | (Lung) NCI-H460 | (Breast) MCF7 | (CNS) SF-268 |
| IX | 0 | 0 | 0 |

[a]One dose of IX at 10$^{-4}$ molar concentration.

The novel pyrrolobenzodiazepine hybrid of formula IX has shown to possess 10 nano molar potency (at the LC50 level) against one non-small cell lung caner (NCI-H522), one CNS cancer (SF-539), three melanoma cancer (SK-MEL-2-SK-MEL-5, VACC-62), two renal cancer (A-498, RXF 393), and one breast cancer (MDA-MB-435). The LC 50 values of nine cancer (average of six to nine cancer cell line) of compound IX listed in Table 3.

TABLE 2 log10 GI50 log10 TGI and LC50 mean graphs midpoints (MG_MID) of in vitro cytotoxicity data for the compound IX as representative compound against human tumour cell lines

| Compound | Log10 GI50 | Log10 TGI | Log10LC50 |
|---|---|---|---|
| V | −7.97 | −6.79 | −4.57 |

TABLE 3

Log LC50 (concentration in mol/L causing 50% lethality) Values for Compounds IX as representative compound.

| Cancer | Compound |
|---|---|
| Leukemia | >4.0 |
| Non-small-cell lung | −4.89 |
| Colon | >−4.03 |
| CNS | −4.12 |
| Melanoma | −5.84 |
| Ovarian | >−4.23 |
| Renal | −4.33 |
| Prostate | −4.48 |
| Breast | >−4.65 |

Each cancer type represents the average of six to nine different cancer cell lines.

TABLE 4
MEAN GRAPH
| Panel/Cell Line | Log₁₀ GI50 | GI50 | Log₁₀ TGI | TGI | Log₁₀ LC50 | LC50 |
|---|---|---|---|---|---|---|
| Leukemia | | | | | | |
| CCRF-CEM | <-8.00 | | <-8.00 | | >-4.00 | |
| K-562 | <-8.00 | | -5.88 | | -4.00 | |
| MOLT-4 | <-8.00 | | <-8.00 | | >-4.00 | |
| RPMI-8226 | <-8.00 | | <-8.00 | | >-4.00 | |
| SR | <-8.00 | | <-8.00 | | >-4.00 | |
| Non-Small Cell Lung Cancer | | | | | | |
| A549/ATCC | <-8.00 | | <-8.00 | | >-4.00 | |
| EKVX | <-8.00 | | -4.96 | | -4.31 | |
| HOP-62 | <-8.00 | | <-8.00 | | -4.79 | |
| NCI-H226 | <-8.00 | | <-8.00 | | -5.39 | |
| NCI-H23 | <-8.00 | | <-8.00 | | >-4.00 | |
| NCI-H322N | <-8.00 | | -6.59 | | >-4.00 | |
| NCI-H460 | <-8.00 | | <-8.00 | | -7.18 | |
| NCI-H522 | <-8.00 | | | | | |
| Colon Cancer | | | | | | |
| COLO-205 | <-8.00 | | >-1.00 | | >-4.00 | |
| HCT-114 | -7.35 | | -4.22 | | >-4.00 | |
| HCT-15 | <-8.00 | | -5.95 | | >-4.00 | |
| HT29 | <-8.00 | | -4.82 | | >-4.00 | |
| KM12 | | | | | -4.23 | |
| SW-620 | | | | | >-4.00 | |
| CNS Cancer | | | | | | |
| SF-263 | <-8.00 | | -6.18 | | -4.11 | |
| SF-295 | <-8.00 | | -6.89 | | >-4.00 | |
| SNB-19 | <-8.00 | | -4.87 | | -4.28 | |
| U251 | | | -5.76 | | -4.12 | |
| Melanoma | | | | | | |
| LOX [MV] | <-8.00 | | -6.72 | | >-4.00 | |
| MALME-3M | <-8.00 | | <-8.00 | | -4.27 | |
| M14 | <-8.00 | | <-8.00 | | -6.44 | |
| SK-MEL-2 | <-8.00 | | <-8.00 | | <-8.00 | |
| SK-MEL-2E | | | | | -5.34 | |
| SK-MEL-5 | | | | | | |
| UACC-62 | -7.75 | | -7.40 | | -7.04 | |
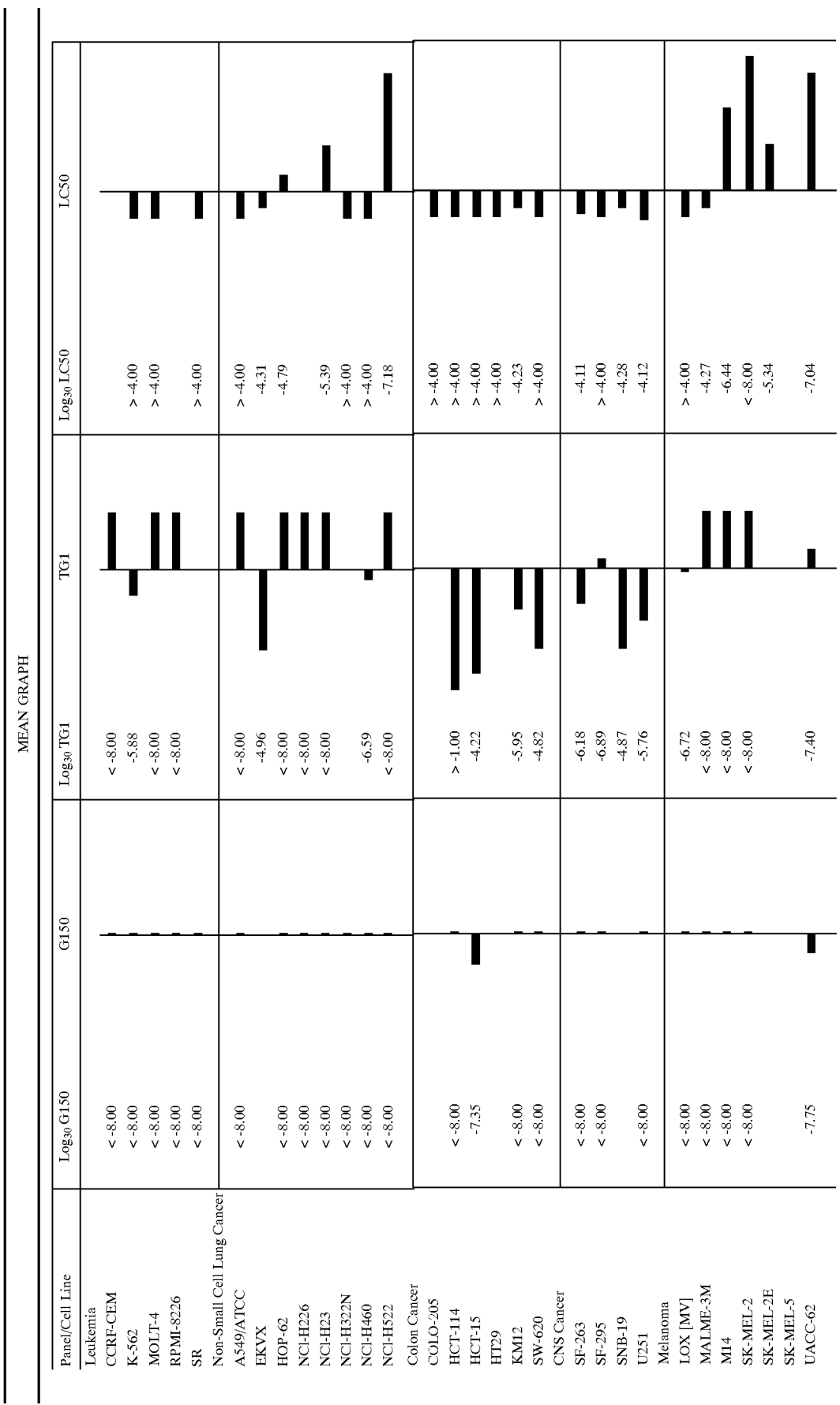

TABLE 4-continued
MEAN GRAPH
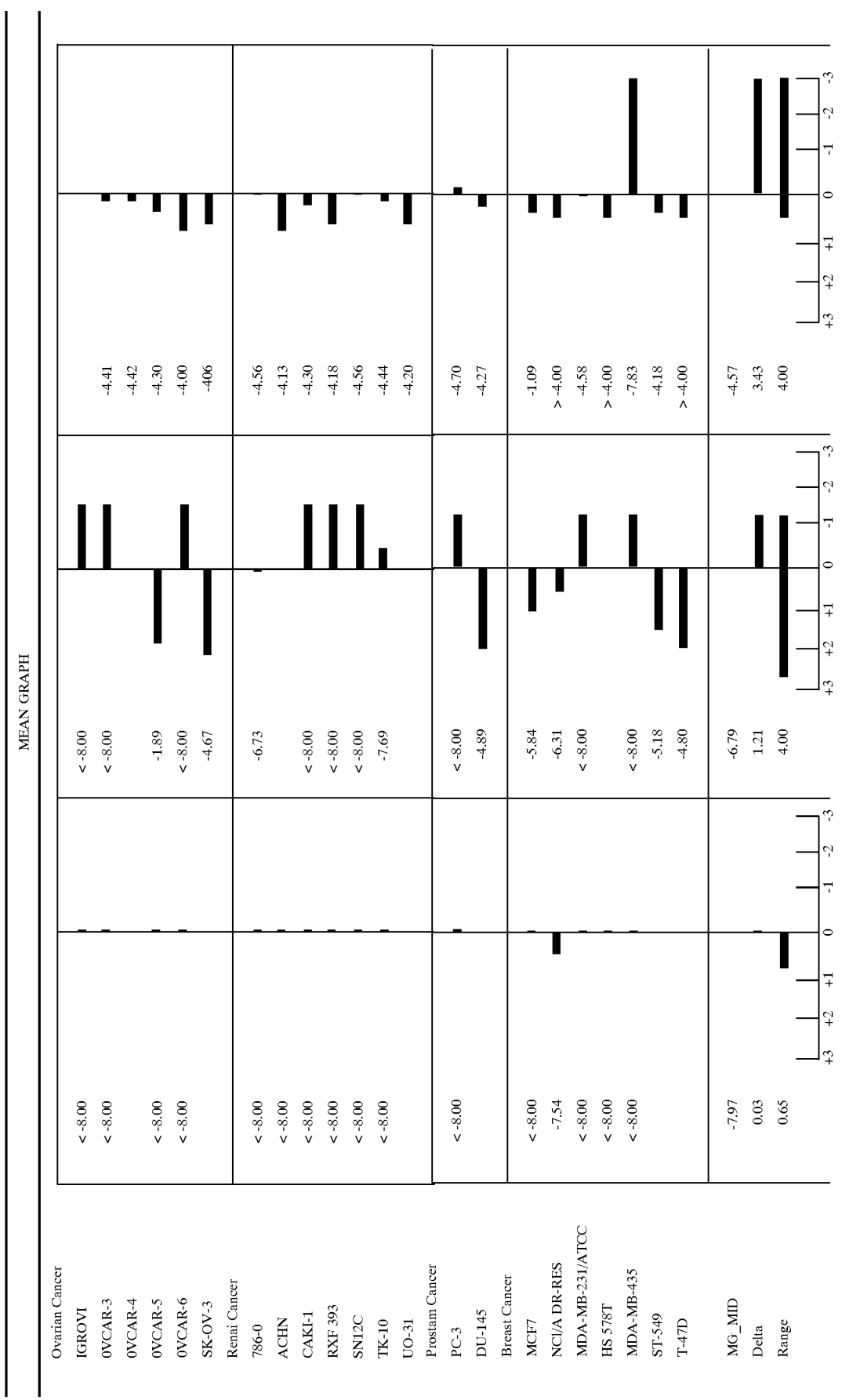
| | | | |
|---|---|---|---|
| Ovarian Cancer | | | |
| IGROVI | <-8.00 | <-8.00 | -4.41 |
| OVCAR-3 | <-8.00 | <-8.00 | -4.42 |
| OVCAR-4 | <-8.00 | -1.89 | -4.30 |
| OVCAR-5 | <-8.00 | <-8.00 | -4.00 |
| OVCAR-6 | <-8.00 | -4.67 | -406 |
| SK-OV-3 | | | |
| Renal Cancer | | | |
| 786-0 | <-8.00 | -6.73 | -4.56 |
| ACHN | <-8.00 | <-8.00 | -4.13 |
| CAKI-1 | <-8.00 | <-8.00 | -4.30 |
| RXF 393 | <-8.00 | <-8.00 | -4.18 |
| SN12C | <-8.00 | <-8.00 | -4.56 |
| TK-10 | <-8.00 | -7.69 | -4.44 |
| UO-31 | | | -4.20 |
| Prostam Cancer | | | |
| PC-3 | <-8.00 | <-8.00 | -4.70 |
| DU-145 | | -4.89 | -4.27 |
| Breast Cancer | | | |
| MCF7 | <-8.00 | -5.84 | -1.09 |
| NCI/A DR-RES | -7.54 | -6.31 | >-4.00 |
| MDA-MB-231/ATCC | <-8.00 | <-8.00 | -4.58 |
| HS 578T | <-8.00 | | >-4.00 |
| MDA-MB-435 | <-8.00 | <-8.00 | -7.83 |
| ST-549 | | -5.18 | -4.18 |
| T-47D | | -4.80 | >-4.00 |
| MG_MID | -7.97 | -6.79 | -4.57 |
| Delta | 0.03 | 1.21 | 3.43 |
| Range | 0.65 | 4.00 | 4.00 |

What is claimed is:

1. A compound of the formula

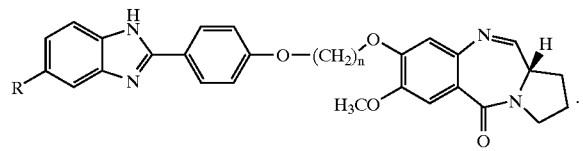

R is H,   n = 3–5

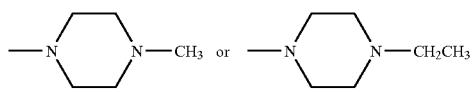

2. The compound as claimed in claim 1 having the formula

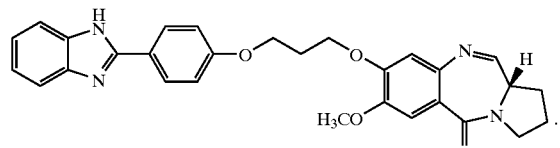

3. The compound as claimed in claim 1 having the formula

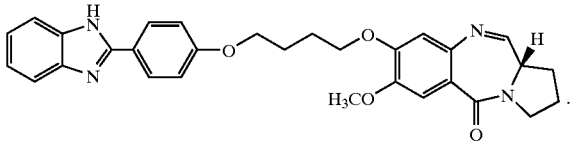

4. The compound as claimed in claim 1 having the formula

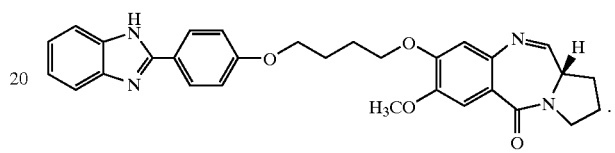

5. The compound as claimed in claim 1 having the formula

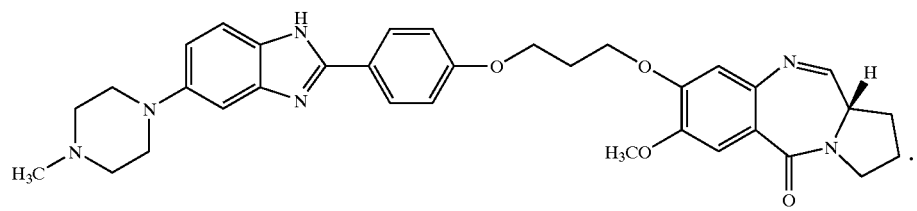

6. The compound as claimed in claim 1 having the formula

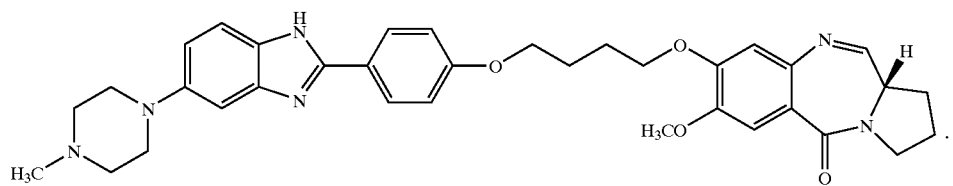

7. The compound as claimed in claim 1 having the formula

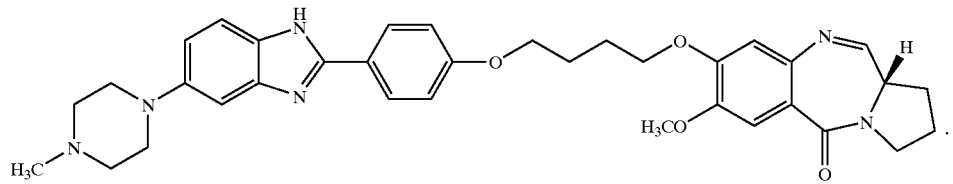

8. The compound as claimed in claim 1 having the formula

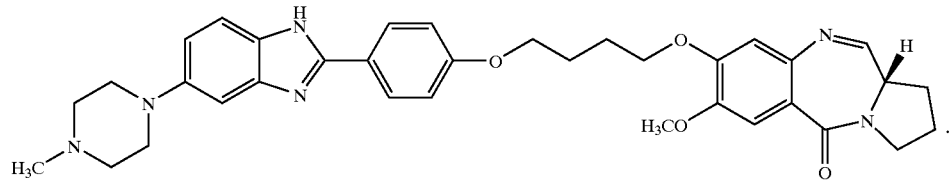

9. The compound as claimed in claim 1 having the formula

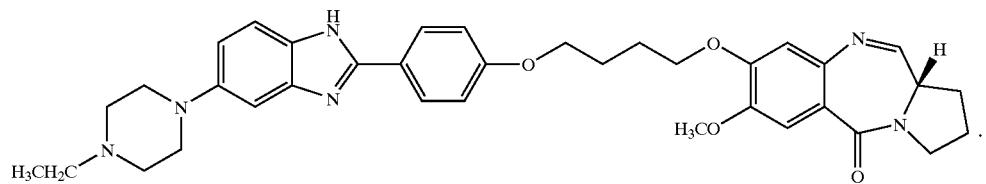

10. The compound as claimed in claim 1 having the formula

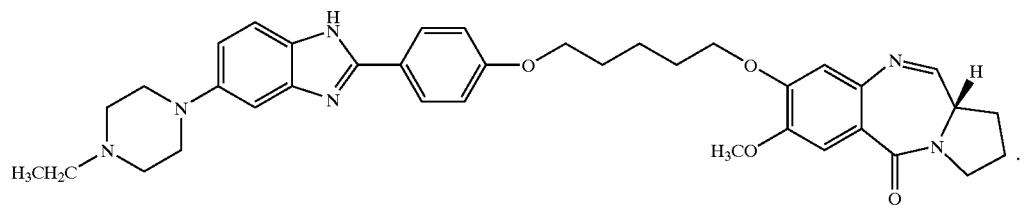

11. A process for the preparation of formula V

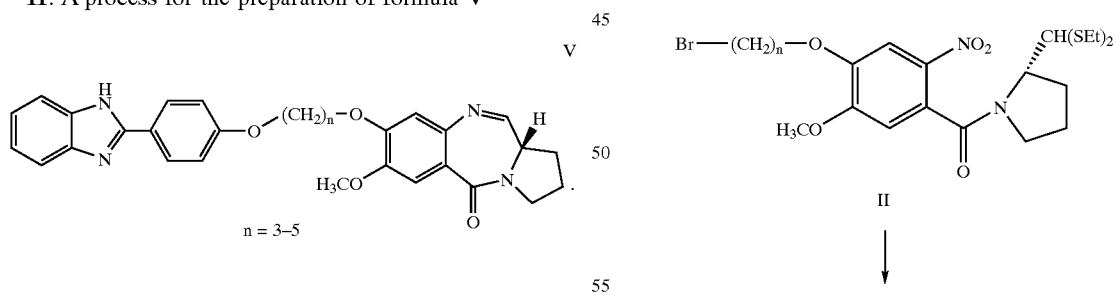

n = 3–5 which comprises reacting a 4-(1H-benzo[d]imidazol-2-yl) phenol of formula I

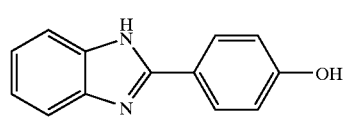

with -[4-(n-bromoalkyloxy)-5-methoxyy-2-nitrobenzo-yl] pyrrolidine-2-carboxaldehyde diethyl thio acetal of formula II in the presence of $K_2CO_3$ in organic solvent for a period of 12 to 24 hrs, isolating (2S)-N-{4-(1H)-benoz[d]imidazolo-2yl)phenoxy]alkyl-oxy-5methoxy-2-nitrobenzoyl}pyrrolidine-2-carboxaldehyde diethyl thioacetal III

III

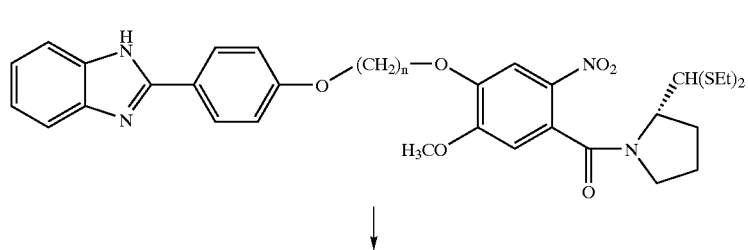

where "n" is 3 to 5, reducing said compound of formula III with $SnCl_2 \cdot 2H_2O$ in the presence of organic solvent up to a reflux temperature, isolating the (2S)-N-{n-4-(1H-benzo[d]imidazolo-2yl)phenoxy]alkyl]-oxy-5-methoxy-2-aminobenzoyly}pyrrolidine-2-carboxaldehyde diethyl thioacetal of formula IV

IV

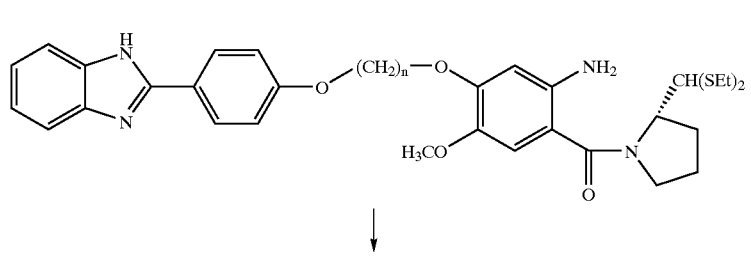

where n is 3 to 5 by known methods, reacting the compound of formula IV with a deprotecting agent to obtain a compound of formula V, wherein n is as defined above.

12. A process for the preparation of formula IX

IX

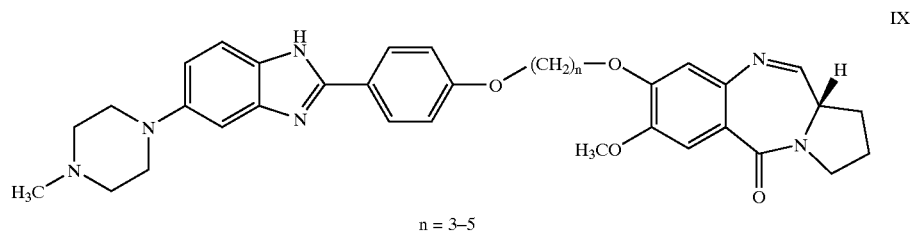

n = 3–5 which comprises reacting a 4-[6-4.-methylhexahydro-1-pyrazinyl-1H-benzo [imidazol-2-yl]phenol VI

VI

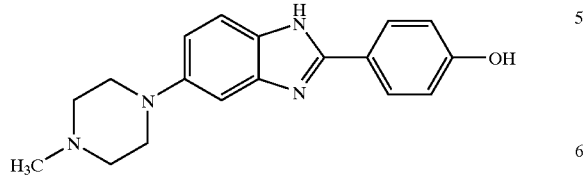

with N-[4-(n-bromoalkyloxy)-5-methoxy-2-nitrobenzo-yl]pyrrolidine-2-carboxaldehyde diethyl thio acetal of formula II

II

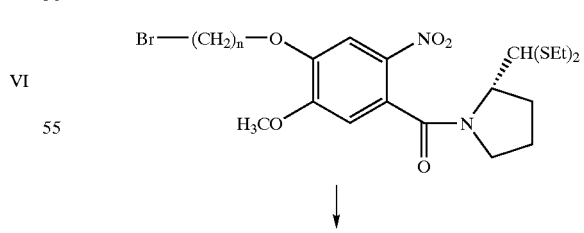

in the presence of $K_2CO_3$ in organic solvent for a period of 12 to 24 hrs, isolating (2S)-N-{n-(4-[6-4-methylhexahydro-1-pyraxinyl)-1H)-benzo[d]imidazol-2yl]phenoxy]alkyl-oxy-5-methoxy-2-nitrobenzoy pyrrolidine-2-carboxaldehyde diethyl thioacetal VII

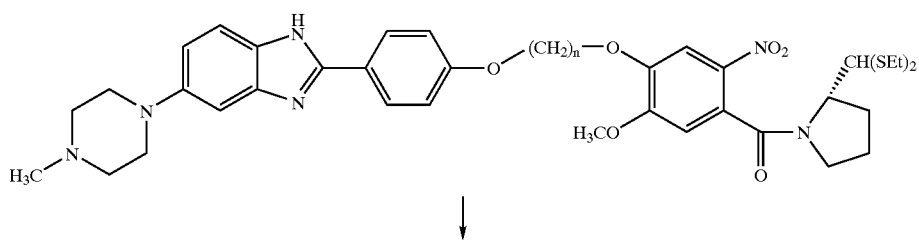

where n is 3 to 5, reducing said compound of formula VII with SnCl2O in the presence of organic solvent up to a reflux temperature, isolating the (2S)-N-{n-(4-[6-(4-methylhexahydro-1-pyrazinyl)-1H-benzo[d]imidazol-2-yl]phenoxy]alkyl)-oxy-5-methoxy-2-aminobenzoy)pyrrolidine-2-carboxaldehyde diethyl thioacetal of formula VIII

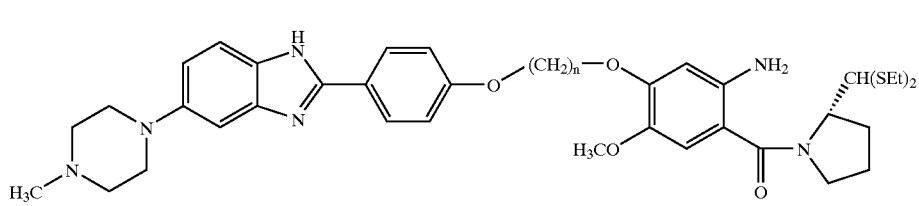

and reacting the compound of formula VIII with a deprotecting agent to produce a compound of formula IX pyrrolo[2,1-c]1,4]benzodiazepine hybrids of formula IX wherein n is as defined above.

13. A process for the preparation of a compound of formula XIII

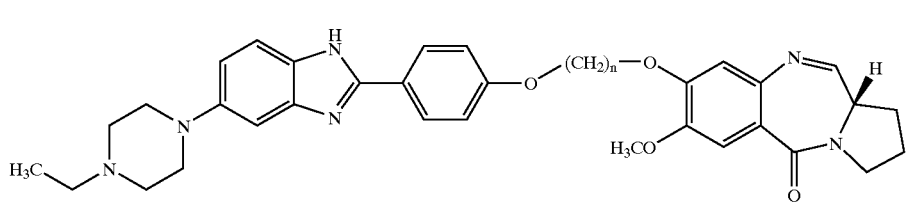

n = 3–5 which comprises reacting a 4-[6-(4-ehtylhexahydro-1-pyrazinyl)-1H-benzo[d]imidazol-2-yl]phenol of formula X

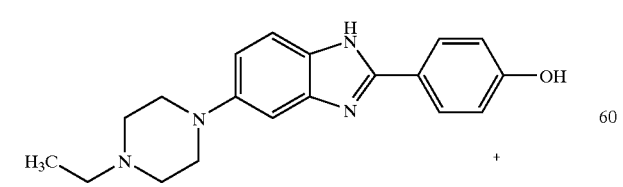

+ with -[4-(n-bromoalkyloxy)-5-methoxyy-2,-nitrobenzo-yl]pyrrolidine-2-carboxaldehyde diethyl thio acetal of formula II

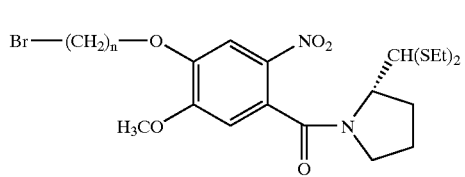

in the presence of K$_2$CO$_3$ in organic solvent for a period of 12 to 24 hrs, isolating (2S)--{n-(4-[6-4-ehtyhexahydro-1-pyrazinyl)-H-benzo[d]imidazol-2-yl]phenoxy]alkyl]-oxy-5-methoxy-2-nitrobenzoyl)pyrrolidine-2-carboxaldehyde diethyl thioacetal of formula XI

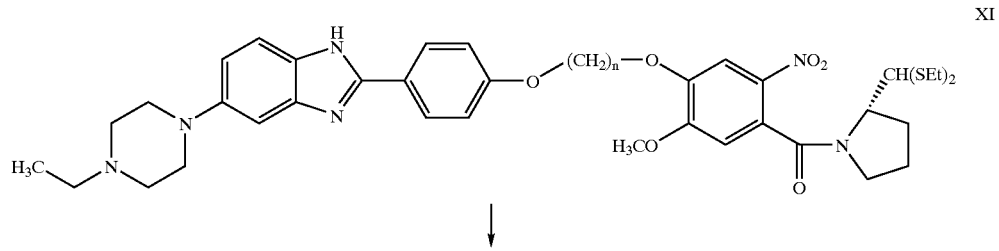

XI where "n" is 3 to 5, reducing said compound of formula XI with SnCl$_2$.2H$_2$O in the presence of organic solvent up to a reflux temperature, isolating (2S)-N-{n-(4-[6-(4-ethylhexahydro-1-pyrazinyl)-1H-benzo[d]imidazol-2-yl]phenoxy]alkyl)-oxy-5-methoxy-2-aminobenzoyl}pyrrolidine-2-carboxaldehyde diethyl thioacetal of formula XII where n is 3 to 5

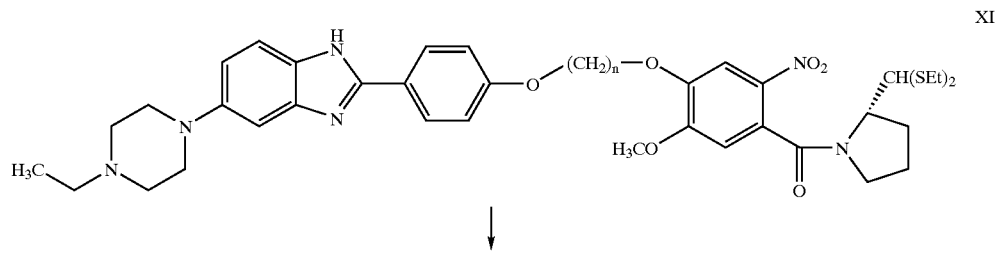

XI and reacting the amino compound of formula XII with a deprotecting agent to produce the compound of formula XIII wherein n is as defined above.

14. A pharmaceutical composition comprising a compound according to claim 1 and an excipient.

15. A method for treating a mammal comprising administering an effective amount of a compound according to claim 1 to the mammal wherein the mammal has at least one cancer selected from the group consisting of leukemia, non-small cell lung, colon, central nervous system, melanoma, ovarian, renal, prostate and breast cancer.

16. A method for treating a mammal comprising administering an effective amount of a composition according to claim 14 to the mammal wherein the mammal has at least one cancer selected from the group consisting of leukemia, non-small cell lung, colon, central nervous system, melanoma, ovarian, renal, prostate and breast cancer.

17. The method according to claim 15 wherein the mammal is a human.

18. The method according to claim 16 wherein the mammal is a human.

* * * * *